United States Patent
Jiang et al.

(10) Patent No.: US 9,809,589 B2
(45) Date of Patent: Nov. 7, 2017

(54) CRYSTAL FORM OF COMPOUND USED AS MINERALOCORTICOID RECEPTOR ANTAGONIST AND PREPARATION METHOD THEREFOR

(71) Applicant: KBP BIOSCIENCES CO., LTD., Jinan, Shandong (CN)

(72) Inventors: Chen Jiang, Jinan (CN); Aichen Wang, Jinan (CN); Dedong Zhang, Jinan (CN)

(73) Assignee: KBP BIOSCIENCES CO., LTD., Jinan, Shandong Province (CN)

( * ) Notice: Subject to any disclaimer, the term of this patent is extended or adjusted under 35 U.S.C. 154(b) by 0 days.

(21) Appl. No.: 14/653,933

(22) PCT Filed: Dec. 23, 2013

(86) PCT No.: PCT/CN2013/090252
§ 371 (c)(1),
(2) Date: Jun. 19, 2015

(87) PCT Pub. No.: WO2014/094664
PCT Pub. Date: Jun. 26, 2014

(65) Prior Publication Data
US 2015/0336950 A1    Nov. 26, 2015

(30) Foreign Application Priority Data
Dec. 22, 2012 (CN) .......................... 2012 1 0563636

(51) Int. Cl.
| | | |
|---|---|---|
| C07D 471/04 | (2006.01) | |
| C07D 215/20 | (2006.01) | |
| C07D 215/60 | (2006.01) | |
| C07D 215/48 | (2006.01) | |
| C07C 255/50 | (2006.01) | |

(52) U.S. Cl.
CPC .......... *C07D 471/04* (2013.01); *C07C 255/50* (2013.01); *C07D 215/20* (2013.01); *C07D 215/48* (2013.01); *C07D 215/60* (2013.01)

(58) Field of Classification Search
CPC ........................... C07D 471/04; C07C 255/50
USPC .......................................................... 546/79
See application file for complete search history.

(56) References Cited

U.S. PATENT DOCUMENTS

2013/0289029 A1    10/2013    Huang et al.

FOREIGN PATENT DOCUMENTS

| WO | 9809969 | 3/1998 |
| WO | 2004048378 A1 | 6/2004 |
| WO | 2012022121 | 2/2012 |

OTHER PUBLICATIONS

Qiu, et al, "Developing Solid Oral Dosage Forms-Pharmaceutical Theory and Practice", Academic Press, Dec. 19, 2008, 2 pages.
Yoshioka, et al., "Stability of Drugs and Dosage Forms", Stability of Drugs and Dosage Forms, Springer Science & Business Media, Jan. 1, 2000, pp. 107-108, 2 pages.
Byrn, et al., Pharmaceutical Solids: A Strategic Approach to Regulatory Considerations, Pharmaceutical Research, 1995, 12(7): 945-954.
EP13864994.2, "Extended European Search Report", dated Aug. 9, 2016, 7 pages.
CN201380055871.7, "Notice to Grant Patent Right for Invention with English translation", dated Sep. 5, 2016, 5 pages.
JP2015-548180 Office Action dated Nov. 21, 2016 with English translation, 9 pages.
RU2015130222 Office Action dated Oct. 14, 2016 with English translation, 13 pages.
Organic Compound Crystallization Preparation Manual with English summary, 29 pages.
International Application No. PCT/CN2013/090252, International Search Report, dated Mar. 27, 2014.

*Primary Examiner* — Rita Desai
(74) *Attorney, Agent, or Firm* — Kilpatrick Townsend & Stockton LLP

(57) ABSTRACT

The present invention belongs to the technical field of medicines, and relates to a crystal form of a compound used as a mineralocorticoid receptor antagonist and a preparation method therefor, and in particular, to a method for preparing a compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile of formula (1); a crystal form thereof, a preparation method for the crystal form, and the use of the crystal form in the preparation of drugs for the treatment and/or prevention of renal injury or cardiovascular diseases.

Formula (1)

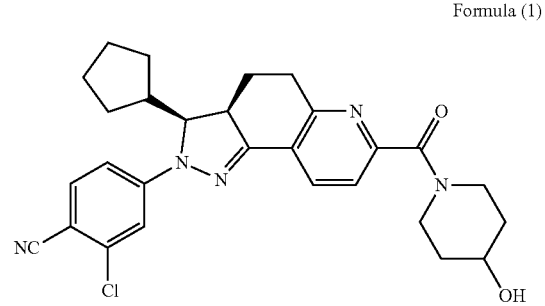

16 Claims, 4 Drawing Sheets

CRYSTAL FORM OF COMPOUND USED AS MINERALOCORTICOID RECEPTOR ANTAGONIST AND PREPARATION METHOD THEREFOR

PRIOR RELATED APPLICATIONS

This application is a National Phase application of International Application No. PCT/CN2013/090252, filed Dec. 23, 2013, which claims priority to Chinese Application No. 201210563636.8, filed on Dec. 22, 2012, which are both incorporated herein by reference in their entireties.

TECHNICAL FIELD

The present invention belongs to the field of pharmaceutical technology. More specifically, the present invention relates to crystal forms of a compound as mineralocorticoid receptor antagonist, a method for preparing the same, and use of crystal forms of the compound in manufacture of a medicament for treating and/or preventing kidney injury or cardiovascular disease.

BACKGROUND

Aldosterone is a mineralocorticoid hormone synthesized at the adrenal cortex, and can bind to the mineralocorticoid receptor and activate the receptor to promote the conservation of sodium and the excretion of potassium. It may have an important role in keeping the electrolyte balance and changing the structure and function of endothelial cells, vascular smooth muscle cells and fibroblasts on the arterial wall as well as the arterial adventitia and the matrix on its media. The high level of aldosterone may result in the abnormal activation of the mineralocorticoid receptor, which can cause the electrolyte imbalance, the blood vessel injury, the fibrosis and the like, and result in the cardiovascular disease such as hypertension, the injury to the organ such as kidney, heart and brain, the endocrine disturbance and the like. A drug that blocks the binding of aldosterone and the mineralocorticoid receptor by competitively binding to the mineralocorticoid receptor can therefore inhibit the aldosterone-mediated injury and reduce the occurrence of the above mentioned disease.

The compound represented by Formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile, as disclosed in the application WO2012022121, is an aldosterone receptor antagonist, which can selectively bind to the mineralocorticoid receptor, and has a lower affinity to the glucocorticoid and the androgen receptor.

Formula (1)

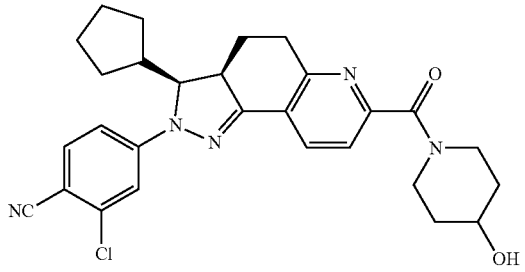

WO2012022121 discloses a process for preparing the compound represented by formula (1), which is obtained by chirally resolving the racemic mixture containing the compound represented by formula (1) following by the rotary-evaporation to dryness. The obtained compound is in the amorphous form.

The compound of formula (1) has two chiral centers. In order to obtain a single isomer, those skilled in the art will resolve the racemic mixture. According to WO2012022121, the racemic mixture containing the compound represented by formula (1) is firstly obtained, and then resolved to obtain the compound represented by formula (1), which makes it difficult to produce the compound represented by formula (1) in a GMP standard plant, resulting in the difficulty in the industrialization and the higher production cost.

SUMMARY OF THE INVENTION

The study on the crystal form is very important in the drug development. Different crystal forms of a compound will result in the difference in the property such as the stability and the solubility. Therefore, the present inventors have conducted many researches on the crystal form of the compound represented by formula (1), and identified and found some useful crystal forms of the compound of Formula (1).

In the preparation of the compound of Formula (1), the present inventors have performed the resolution step in advance so that it can be easy to produce the compound represented by formula (1) in a GMP standard workshop and the industrialization can be smoothly accomplished.

The first object of the present invention is to provide crystal forms of the compound of Formula (1).

The second object of the present invention is to provide a process for preparing the compound of Formula (1).

The third object of the present invention is to provide a process for preparing crystal forms of the compound of Formula (1) and a method for converting any one of crystal forms into another crystal form.

Another object of the present invention is to provide use of crystal forms of the compound of Formula (1) for treating and/or preventing kidney injury or cardiovascular disease (including heart injury, hypertension, heart failure, myocardial infarction, angina pectoris, cardiac hypertrophy, myocarditis, fibrosis of heart and blood vessel, baroceptor dysfunction or arrhythmia), and use of crystal forms of the compound of Formula (1) in manufacture of a medicament for treating and/or preventing kidney injury or cardiovascular disease (including heart injury, hypertension, heart failure, myocardial infarction, angina pectoris, cardiac hypertrophy, myocarditis, fibrosis of heart and blood vessel, baroceptor dysfunction or arrhythmia).

The technical solutions according to the present invention are as follows:

1. Crystal form of a compound represented by formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile

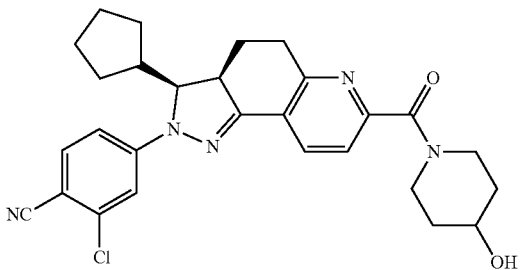

(1)

which is characterized by having an X-ray powder diffraction pattern comprising the following characteristic peaks expressed by 2θ degree, when measured using CuKa radiation:

Crystal Form I: 14.8°±0.2°, 17.4°±0.2°, 19.4°±0.2°, 19.8°±0.2°;
Crystal Form II: 14.6°±0.2°, 19.9°±0.2°, 21.2°±0.2°, 24.6°±0.2°;
Crystal Form III: 15.3°±0.2°, 19.5°±0.2°, 20.5°±0.2°, 25.0°±0.2°.

2. Crystal form of the compound according to Solution 1, which is characterized by having an X-ray powder diffraction pattern comprising the following characteristic peaks expressed by 2θ degree, when measured using CuKa radiation:

Crystal Form I: 14.8°±0.2°, 16.9°±0.2°, 17.4°±0.2°, 19.4°±0.2°, 19.8°±0.2°, 26.2°±0.2°;
Crystal Form II: 14.6°±0.2°, 18.0°±0.2°, 18.7°±0.2°, 19.9°±0.2°, 21.2°±0.2°, 24.6°±0.2°;
Crystal Form III: 10.0°±0.2°, 15.3°±0.2°, 15.8°±0.2°, 19.5°±0.2°, 20.5°±0.2°, 25.0°±0.2°.

3. Crystal form of the compound according to Solution 1 or 2, which is characterized by having an X-ray powder diffraction pattern comprising the following characteristic peaks expressed by 2θ degree, when measured using CuKa radiation:

Crystal Form I: 9.8°±0.2°, 12.9°±0.2°, 14.8°±0.2°, 15.4°±0.2°, 16.9°±0.2°, 17.4°±0.2°, 19.4°±0.2°, 19.8°±0.2°, 22.6°±0.2°, 26.2°±0.2°;
Crystal Form II: 4.5°±0.2°, 9.0°±0.2°, 12.2°±0.2°, 14.0°±0.2°, 14.6°±0.2°, 18.0°±0.2°, 18.7°±0.2°, 19.9°±0.2°, 21.2°±0.2°, 24.6°±0.2°;
Crystal Form III: 3.8°±0.2°, 10.0°±0.2°, 15.3°±0.2°, 15.8°±0.2°, 17.9°±0.2°, 19.5°±0.2°, 20.5°±0.2°, 25.0°±0.2°, 26.0°±0.2°, 27.2°±0.2°.

4. A process for preparing a compound represented by formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile,

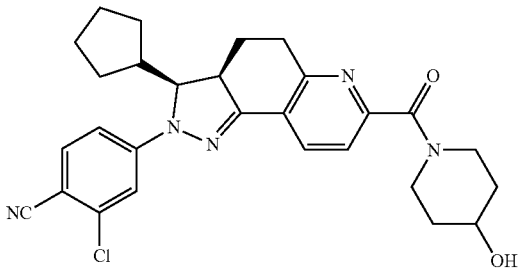

(1)

which is characterized by comprising the steps of:

(9) Chirally resolving ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-ethyl 2-(3-chloro-4-cyanophenyl)-3-cyclopentyl-3,3a,4,5-tetrahydro-2H-pyrazolo[3,4-f]quinoline-7-carboxylate;

(10) Hydrolyzing (3S,3aR)-ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-2-(3-chloro-4-cyanophenyl)-3-cyclopentyl-3,3a,4,5-tetrahydro-2H-pyrazolo[3,4-f]quinoline-7-carboxylic acid;

(11) Subjecting (3S,3aR)-2-(3-chloro-4-cyanophenyl)-3-cyclopentyl-3,3a,4,5-tetrahydro-2H-pyrazolo[3,4-f]quinoline-7-carboxylic acid and 4-hydroxypiperidine to a condensation reaction to produce the compound represented by formula (1).

5. The process of Solution 4, further comprising one of the following steps:

placing the compound represented by formula (1) obtained in the step (11) in an anhydrous lower alcohol, acetonitrile, a mixed solvent of ethyl acetate and ethanol, a mixed solvent of methanol and tetrahydrofuran, or a mixed solvent of acetonitrile and acetone, heating the resulting solution until it becomes clear, then cooling the resulting solution to separate out a solid, and filtering and drying the separated solid; or placing the compound represented by formula (1) obtained in the step (11) in a lower alcohol to dissolve it, then adding the resulting solution dropwisely to water, filtering the resulting mixture, and optionally drying the filtered substance under vacuum; or washing the compound represented by formula (1) obtained in the step (11) with a mixed solution of water and acetonitrile, filtering the resulting mixture, and optionally drying the filtered substance under vacuum; or dissolving the compound represented by formula (1) obtained in the step (11) in acetone, adding the resulting solution dropwisely to n-heptane, and filtering the resulting mixture.

5-1. The process according to Solution 4 or 5, further comprising the step (8) immediately before the step (9):

(8) Subjecting (E)-ethyl 6-cyclopentylmethylene-5-oxo-5,6,7,8-tetrahydroquinoline-2-carboxylate and 2-chloro-4-hydrazinobenzonitrile hydrochloride to a condensation reaction to produce ethyl 2-(3-chloro-4-cyanophenyl)-3-cyclopentyl-3,3a,4,5-tetrahydro-2H-pyrazolo[3,4-f]quinoline-7-carboxylate.

5-2. The process according to Solution 5-1, further comprising the step (7) immediately before the step (8):

(7) Subjecting 2-chloro-4-hydrazinobenzonitrile and hydrochloric acid to a salt forming reaction to produce 2-chloro-4-hydrazinobenzonitrile hydrochloride.

5-3. The process according to Solution 5-2, further comprising the step (6) immediately before the step (7):

(6) Subjecting 2-chloro-4-fluorobenzonitrile and hydrazine hydrate to a substitution reaction to produce 2-chloro-4-hydrazinobenzonitrile.

5-4. The process according to Solution 5-3, further comprising the step (5) immediately before the step (6):

(5) Subjecting ethyl 5-oxo-5,6,7,8-tetrahydroquinoline-2-carboxylate and cyclopentanecarbaldehyde to a condensation reaction to produce (E)-ethyl 6-cyclopentylmethylene-5-oxo-5,6,7,8-tetrahydroquinoline-2-carboxylate.

5-5. The process according to Solution 5-4, further comprising the step (4) immediately before the step (5):
(4) Subjecting 5-oxo-5,6,7,8-tetrahydroquinoline-2-carbonitrile to hydrolysis and esterification reactions to produce ethyl 5-oxo-5,6,7,8-tetrahydroquinoline-2-carboxylate.

5-6. The process according to Solution 5-5, further comprising the step (3) immediately before the step (4):
(3) Subjecting 5-oxo-5,6,7,8-tetrahydroquinoline-N-oxide, N,N-dimethylcarbamic chloride, and trimethylsilylcyanide to a substitution reaction to produce 5-oxo-5,6,7,8-tetrahydroquinoline-2-carbonitrile.

5-7. The process according to Solution 5-6, further comprising the step (2) immediately before the step (3):
(2) Subjecting 5-oxo-5,6,7,8-tetrahydroquinoline to an oxidation reaction to produce 5-oxo-5,6,7,8-tetrahydroquinoline-N-oxide.

5-8. The process according to Solution 5-7, further comprising the step (1) immediately before the step (2):
(1) Subjecting 1,3-cyclohexanedione, ammonium acetate and acrolein to condensation and addition reactions to produce 5-oxo-5,6,7,8-tetrahydroquinoline.

6. A process for preparing Crystal Form I of the compound represented by formula (1) according to Solution 1, 2 or 3, which is characterized by, placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in an anhydrous lower alcohol, acetonitrile, a mixture of ethyl acetate and ethanol, a mixture of methanol and tetrahydrofuran, or a mixture of acetonitrile and acetone, heating the resulting solution until it becomes clear, then cooling the resulting solution to separate out a solid, and filtering and drying the separated solid to produce Crystal Form I; or dissolving the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in acetone, adding the resulting solution dropwisely to n-heptane, and filtering the resulting mixture to produce Crystal Form I.

7. A process for preparing Crystal Form III of the compound represented by formula (1) according to Solution 1, 2 or 3, which is characterized by, placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in a lower alcohol to dissolve it, then adding the resulting solution dropwisely to water, and filtering the resulting mixture to produce the resulting Crystal Form III; or washing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile with a mixture of water and acetonitrile, and filtering the resulting mixture to produce the resulting Crystal Form III.

8. A process for preparing Crystal Form II of the compound represented by formula (1) according to Solution 1, 2 or 3, which is characterized by, placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in a lower alcohol to dissolve it, then adding the resulting solution dropwisely to water, and filtering the resulting mixture to produce the resulting Crystal Form III; or washing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile with a mixture of water and acetonitrile, and filtering the resulting mixture to produce the resulting Crystal Form III; then drying the resulting Crystal Form III under vacuum to produce Crystal Form II.

According to the present invention, the term "lower alcohol" refers to methanol, ethanol, n-propanol and the like.

9. A pharmaceutical composition, which is characterized in that said pharmaceutical composition contains the crystal form of the compound represented by formula (1) of Solution 1, 2 or 3, and a pharmaceutically acceptable carrier, wherein said crystal form comprises Crystal Forms I, II and III or a combination thereof.

9-1. The present invention also provides a pharmaceutical composition containing Crystal Forms I, II and III of the compound represented by formula (1) or a combination thereof. Said pharmaceutical composition can also contain a pharmaceutically acceptable carrier, such as excipient, binder, humidifier, disintegrant, thickener and the like.

10. Use of the crystal form of the compound represented by formula (1) according to Solution 1, 2 or 3 in manufacture of a medicament for treating and/or preventing kidney injury or cardiovascular disease, wherein said crystal form comprises Crystal Forms I, II, III or a combination thereof.

11. Use of Solution 10, wherein said cardiovascular disease comprises heart injury, hypertension, heart failure, myocardial infarction, angina pectoris, cardiac hypertrophy, myocarditis, fibrosis of heart and blood vessel, baroceptor dysfunction or arrhythmia.

12. A method of treating and/or preventing kidney injury or cardiovascular disease, wherein said method comprises administrating a subject in need thereof a therapeutically effective amount of the crystal form of the compound represented by formula (1) according to Solution 1, 2 or 3, wherein said crystal form comprises Crystal Forms I, II, III or a combination thereof.

13. The method of Solution 12, wherein said cardiovascular disease comprises heart injury, hypertension, heart failure, myocardial infarction, angina pectoris, cardiac hypertrophy, myocarditis, fibrosis of heart and blood vessel, baroceptor dysfunction or arrhythmia.

14. The crystal form of the compound represented by formula (1) according to Solution 1, 2 or 3 for treating and/or preventing kidney injury or cardiovascular disease, wherein said crystal form comprises Crystal Forms I, II, III or a combination thereof.

15. The crystal form according to Solution 14, wherein said cardiovascular disease comprises heart injury, hypertension, heart failure, myocardial infarction, angina pectoris, cardiac hypertrophy, myocarditis, fibrosis of heart and blood vessel, baroceptor dysfunction or arrhythmia.

16. Crystal Forms I, II and III and the amorphous form of the compound represented by formula (1) can be converted with each other under a certain condition. The present invention also provides the conversion among Crystal Form I, Crystal Form II, Crystal Form III and the amorphous form.

The amorphous form can be recrystallized in anhydrous ethanol to produce Crystal Form I;

Crystal Forms I, II and III or a combination thereof can be dissolved in a lower alcohol as solvent, and then rotary-evaporated to dryness to produce the amorphous form;

Crystal Form II can be recrystallized in anhydrous ethanol to produce Crystal Form I;

The amorphous form can be dissolved in methanol, and the resulting solution is then added dropwisely to water to produce Crystal Form III;

Crystal Form III can be dried at room temperature to produce Crystal Form II;

Crystal Form I can be washed with a system of acetonitrile and water to produce Crystal Form III; and Crystal Form III can be recrystallized in anhydrous ethanol to produce Crystal Form I.

DESCRIPTION OF THE DRAWINGS

FIG. 4: the conversion relation among Crystal Form I, Crystal Form II, Crystal Form III and the amorphous form of the compound of Formula (1), wherein:

Figure 1:
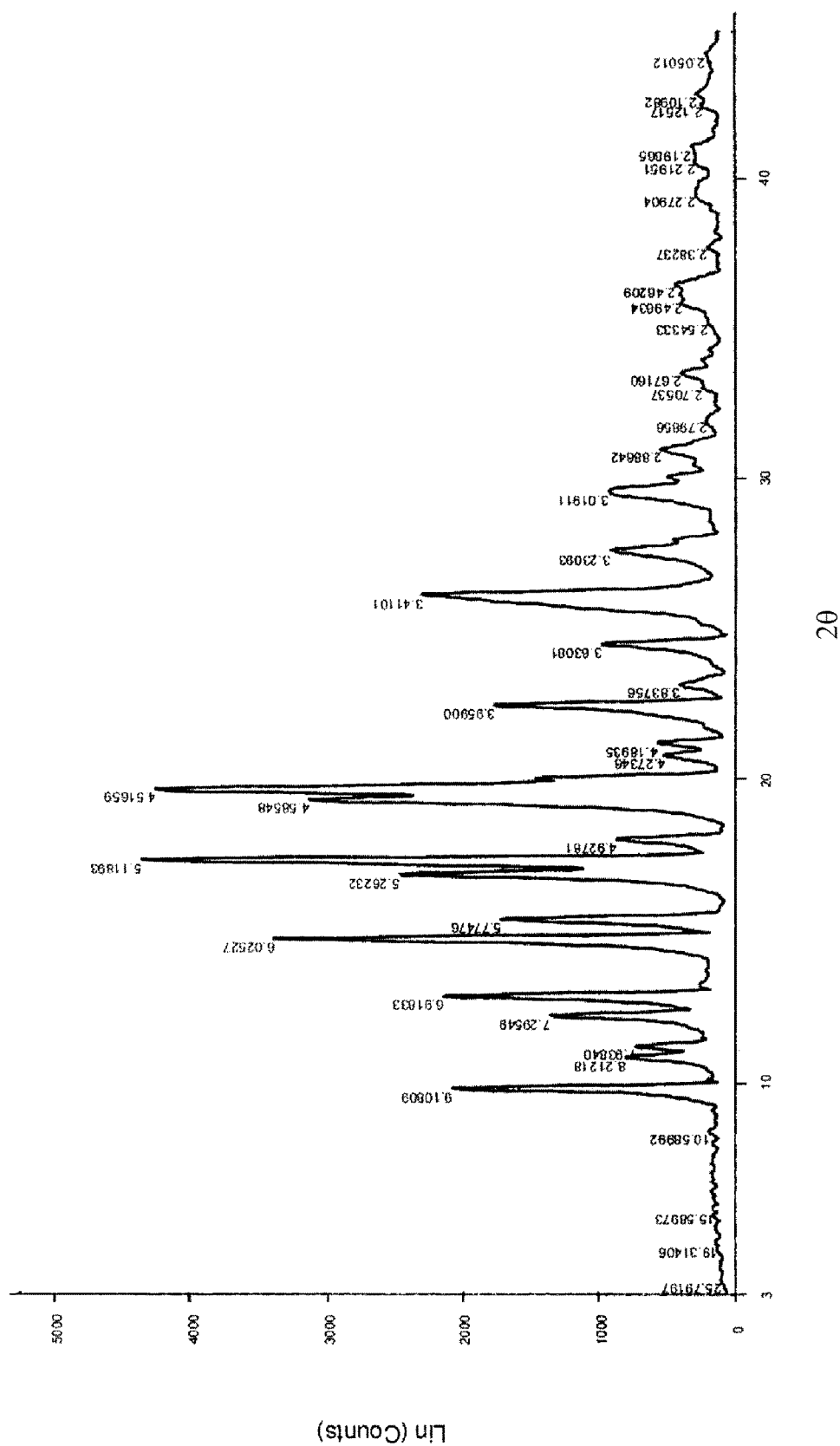
FIG. 1: the XRD spectrum for Crystal Form I of the compound of Formula (1)

1. Being recrystallized with ethanol;
2. Being dissolved in a lower alcohol and then rotary-evaporated to dryness;
3. Being dissolved in methanol, and then separated out with the addition of water;
4. Being dissolved in a lower alcohol and then rotary-evaporated to dryness;
5. Being dissolved in a lower alcohol and then rotary-evaporated to dryness;
6. Being recrystallized with ethanol;
7. Being washed with acetonitrile/water;
8. Being recrystallized with ethanol;
9. Being dried at room temperature.

EMBODIMENTS

The present invention will be illustrated in details by the following embodiments in form of Examples. However, it should be understood that the scope of the present invention is not limited by the following Examples.

Example 1: Preparation of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile

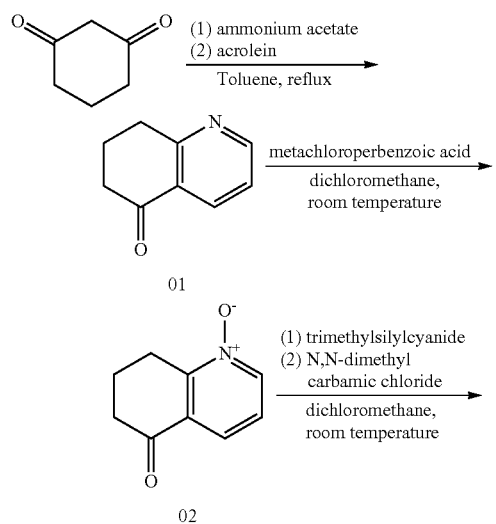

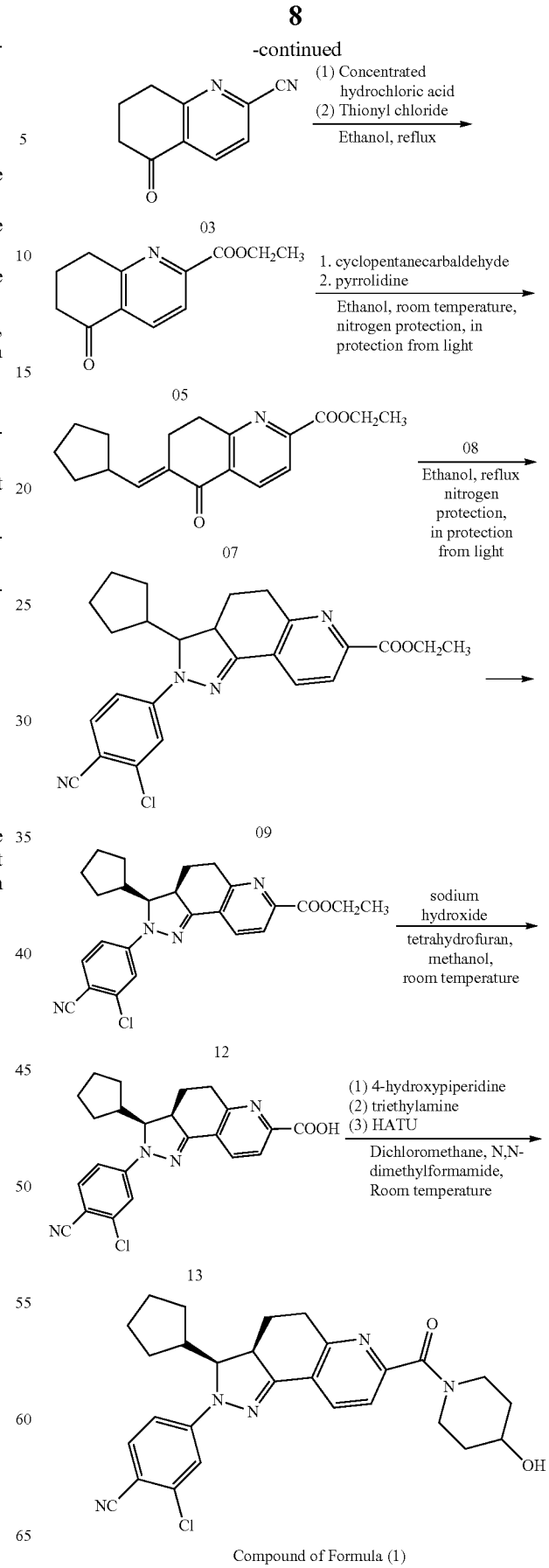

Compound of Formula (1)

-continued

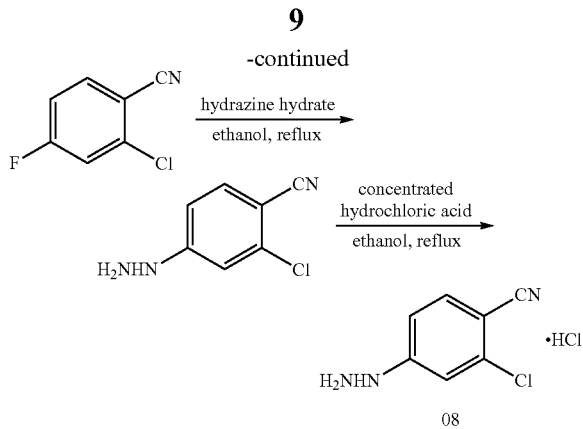

1. Preparation of 5-oxo-5,6,7,8-tetrahydroquinoline (01)

Reaction Equation:

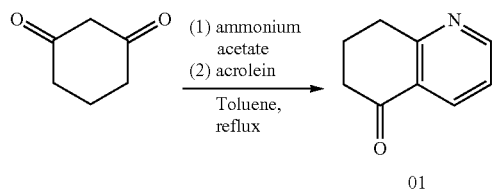 [SMILES: O=C1CCCC(=O)C1 ; O=C1CCCc2ncccc21]

Two Reactions were Conducted in Parallel:

To a 100 L reaction vessel was added toluene (45 L), and then added 1,3-cyclohexanedione (15 kg) under stirring. The resulting mixture was heated until the solid was dissolved. To the resulting solution was added ammonium acetate (24 kg). The resulting mixture was heated to reflux for 12 hours, and cooled to 0° C. To the resulting mixture was slowly added a total of 15 kg of acrolein in batches. The mixture was slowly warmed to reflux, reacted for 12 hours, cooled, and separated into layers. The lower layer was washed with toluene twice (5 L×2). The organic layers were combined and concentrated to dryness to give a total of 7.4 kg of crude 5-oxo-5,6,7,8-tetrahydroquinoline as a black liquid, yield: 18.8%.

2. Preparation of 5-oxo-5,6,7,8-tetrahydroquinoline-N-oxide (02)

Reaction Equation:

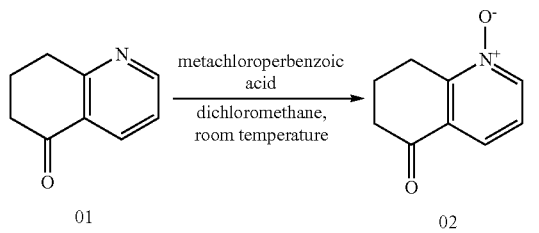 [SMILES: O=C1CCCc2ncccc21 ; O=C1CCCc2c1ccc[n+]2[O-]]

The crude 5-oxo-5,6,7,8-tetrahydroquinoline (7.4 kg) was charged to a 100 L reaction vessel. Dichloromethane was added to the reaction vessel to the total volume of 50 L. The resulting mixture was cooled to −10° C. Metachloroperbenzoic acid (13 kg) was added in batches. Then the mixture was stirred for 20 hours at room temperature. The reaction mixture was then filtered by suction. The filter cake was washed with dichloromethane twice and combined with the filtrate. The organic solution was washed with a saturated sodium thiosulfate solution to such a level that the potassium iodide starch test paper no more showed blue and dried with anhydrous sodium sulfate to produce a solution (50 L), which was not further treated and directly used for the next step.

3. Preparation of 5-oxo-5,6,7,8-tetrahydroquinoline-2-carbonitrile (03)

Reaction Equation:

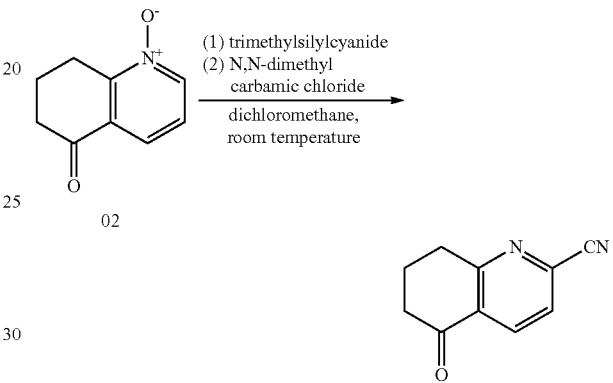

To a 100 L reaction vessel was added the above solution of 5-oxo-5,6,7,8-tetrahydro-quinoline-N-oxide (50 L), then added trimethylsilylcyanide (10 kg), and then slowly added N,N-dimethylcarbamic chloride (11 kg). The reaction mixture was stirred at room temperature for 48 hours. A saturated aqueous sodium hydroxide solution was slowly added in batch to adjust the pH to 8-9. The resulting mixture was separated into layers, and extracted. The aqueous phase was extracted with dichloromethane for three times (8 L×3). The organic phases were combined, and washed with water once (20 L). The resulting organic phase was dried over anhydrous sodium sulfate, filtered, and concentrated under reduced pressure to give a red-black liquid (about 8 L). The liquid was cooled and crystallized with ethanol to produce 5-oxo-5,6,7,8-tetrahydroquinoline-2-carbonitrile (930 g), yield: 10.7% (calculated based on the starting material of 5-oxo-5,6,7,8-tetrahydroquinoline).

4. Preparation of ethyl 5-oxo-5,6,7,8-tetrahydroquinoline-2-carboxylate (05)

Reaction Equation:

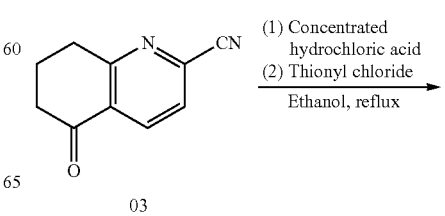

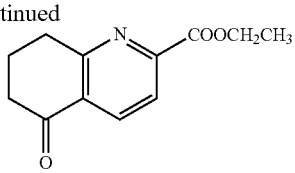

Three Reactions were Conducted in Parallel:

To a 2 L round-bottom flask were added anhydrous ethanol (800 mL) and 5-oxo-5,6,7,8-tetrahydroquinoline-2-carbonitrile (280 g). Then, concentrated hydrochloric acid (400 mL) was added in an ice bath. The mixture was warmed and stirred for 16 hours under reflux. The reaction mixture was then cooled, and concentrated. After adding anhydrous ethanol (1 L), the resulting mixture was cooled to 0° C. After adding dropwisely thionyl chloride (200 mL), the resulting mixture was warmed and stirred for 10 hours under reflux. The reaction mixture was concentrated and the residue was dissolved in dichloromethane. The resulting solution was adjusted with a sodium bicarbonate solution to pH >7, and separated into layers. The aqueous phase was extracted with dichloromethane for three times. The organic phases were combined, dried, concentrated to give ethyl 5-oxo-5,6,7,8-tetrahydroquinoline-2-carboxylate (875 g) altogether, yield: 8.18%.

5. Preparation of (E)-ethyl 6-cyclopentylmethylene-5-oxo-5,6,7,8-tetrahydroquinoline-2-carboxylate (07)

Reaction Equation:

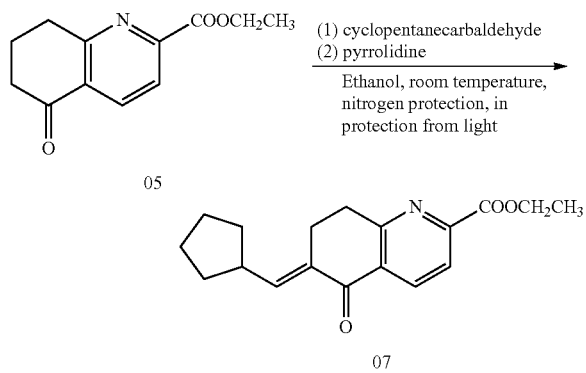

Three Reactions were Conducted in Parallel:

To a 2 L single-necked bottle were added ethyl 5-oxo-5,6,7,8-tetrahydroquinoline-2-carboxylate (291 g) and ethanol (450 mL). Under −20° C., cyclopentanecarbaldehyde (213 mL) was further added, and the resulting mixture was stirred for 10 minutes, then pyrrolidine (110 mL) was slowly added. Under nitrogen protection and protection from light, the reaction was stirred for 8 hours at room temperature. The solution was kept by stand at −20° C. for 2 hours, and filtered. The obtained solid was washed with cooled ethanol and dried to give (E)-ethyl 6-cyclopentylmethylene-5-oxo-5,6,7,8-tetrahydroquinoline-2-carboxylate (862 g), yield: 72.3%.

6. Preparation of 2-chloro-4-hydrazinobenzonitrile hydrochloride (08)

Reaction Equation:

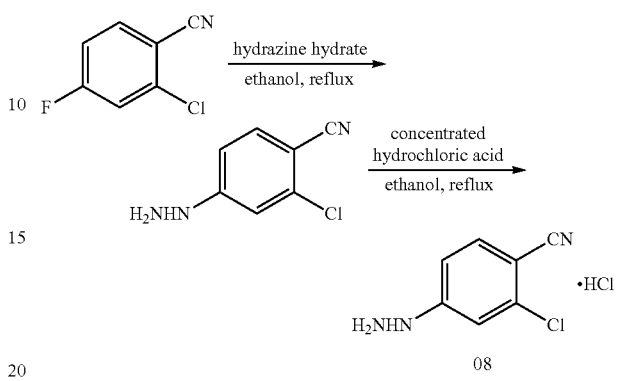

To a 100 L reaction vessel were added ethanol (40 L) and 2-chloro-4-fluorobenzonitrile (7 kg). Then hydrazine hydrate (4 L) was added. The resulting mixture was heated to reflux for 5 hours, then cooled, and subjected to centrifugal filtration. The resulting solid was introduced into a 100 L reaction vessel. Anhydrous ethanol (40 L) was added, and then concentrated hydrochloric acid (7.5 L) was slowly added. The resulting mixture was heated to reflux for 2 hours, subjected to centrifugal filtration, and dried to produce 2-chloro-4-hydrazinobenzonitrile hydrochloride (7 kg), yield: 76.2%.

7. Preparation of ethyl 2-(3-chloro-4-cyanophenyl)-3-cyclopentyl-3,3a,4,5-tetrahydro-2H-pyrazolo[3,4-f]quinoline-7-carboxylate (09)

Reaction Equation:

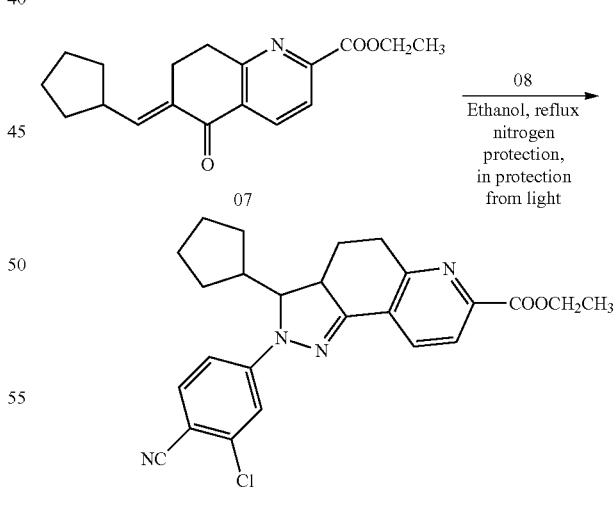

Fours Reactions were Conducted in Parallel:

To a 2 L single-necked bottle were added (E)-ethyl 6-cyclopentylmethylene-5-oxo-5,6,7, 8-tetrahydroquinoline-2-carboxylate (215.5 g), 2-chloro-4-hydrazinobenzonitrile hydrochloride (191 g) and ethanol (900 mL). Under nitrogen protection and protection from light, the reaction was heated to reflux for 9 hours at 80° C., cooled to room temperature, kept by stand under −20° C. for 2 hours, and filtered. The resulting solid was washed with cooled ethanol and diethyl ether respectively, and dried to produce ethyl 2-(3-chloro-4-cyanophenyl)-3-cyclopentyl-3,3a,4,5-tetrahydro-2H-pyrazolo[3,44]quinoline-7-carboxylate (1026 g), yield: 79.3%.

8. Preparation of (3S,3aR)-ethyl 2-(3-chloro-4-cyanophenyl)-3-cyclopentyl-3,3a,4,5-tetrahydro-2H-pyrazolo[3,4-f]quinoline-7-carboxylate (12)

Reaction Equation:

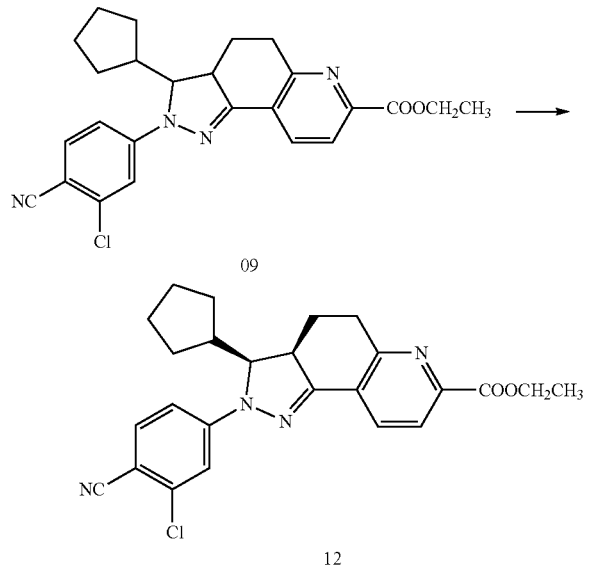

Ethyl 2-(3-chloro-4-cyanophenyl)-3-cyclopentyl-3,3a,4,5-tetrahydro-2H-pyrazolo[3,4-f]quinoline-7-carboxylate was resolved with SFC (supercritical fluid chromatograph) to produce two isomers. The first component obtained by separation and collection was (3S,3aR)-ethyl 2-(3-chloro-4-cyanophenyl)-3-cyclopentyl-3,3a,4,5-tetrahydro-2H-pyrazolo[3,4-f]quinoline-7-carboxylate;

The Resolution Conditions:

Instrument: SFC (Novasep 30-50)

Preparation column: Chiralpak IA, 20 μm, 5×25 cm

Mobile phase: Phase A was supercritical $CO_2$, Phase B was dichloromethane:tetrahydrofuran:diethanolamine=50:50:0.1 (vol:vol:vol), A:B=50:50 (vol:vol)

Flow rate: 150 g/min

Detection wavelength: 465 nm

Sample preparation: ethyl 2-(3-chloro-4-cyanophenyl)-3-cyclopentyl-3,3a,4,5-tetrahydro-2H-pyrazolo[3,4-f]quinoline-7-carboxylate (1025 g) was ultrasonically dissolved in dichloromethane. The resulting mixture was filtered to produce a sample solution (about 50 mg/mL).

The sample solution was resolved with SFC, and the first isomer with an appearance of peak was collected, i.e. (3S,3aR)-ethyl 2-(3-chloro-4-cyanophenyl)-3-cyclopentyl-3,3a,4,5-tetrahydro-2H-pyrazolo[3,4-f]quinoline-7-carboxylate (601.58 g).

9. Preparation of (3S,3aR)-2-(3-chloro-4-cyanophenyl)-3-cyclopentyl-3,3a,4,5-tetrahydro-2H-pyrazolo[3,4-f]quinoline-7-carboxylic acid (13)

Reaction Equation:

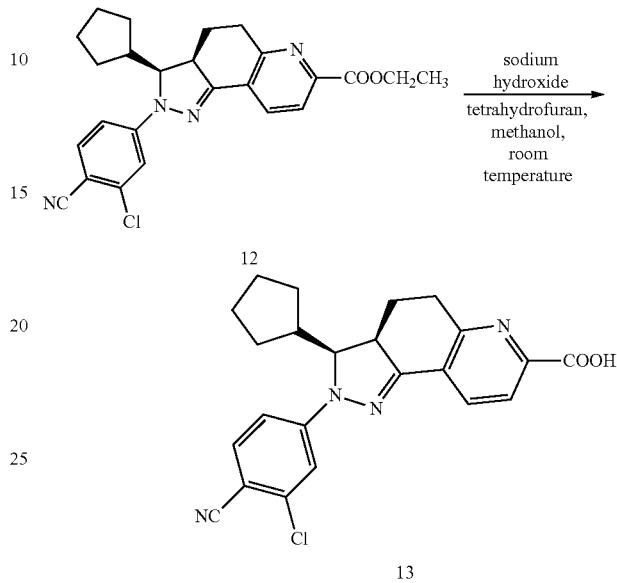

To a 20 L reaction vessel were added (3S,3aR)-ethyl 2-(3-chloro-4-cyanophenyl)-3-cyclopentyl-3,3a,4,5-tetrahydro-2H-pyrazolo[3,4-f]quinoline-7-carboxylate (1066 g), tetrahydrofuran (4 L) and methanol (2 L). The mixture was stirred at −10° C. for 10 minutes, and a solution (1.2 L) of sodium hydroxide (192 g) in water was slowly added thereto. The resulting mixture was stirred at room temperature for 4 hours, and a half of the solvent was removed under vacuum. The reaction mixture was adjusted with dilute hydrochloric acid to pH 3-4, and filtered by suction. The solid was washed with cooled methanol and diethyl ether respectively and dried to produce (3S,3aR)-2-(3-chloro-4-cyanophenyl)-3-cyclopentyl-3,3a,4,5-tetrahydro-2H-pyrazolo[3,4-f]quinoline-7-carboxylic acid (867 g), yield: 86.7%.

10. Preparation of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile (The compound of Formula (1))

Reaction Equation:

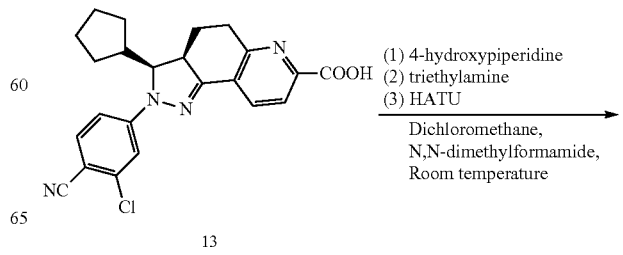

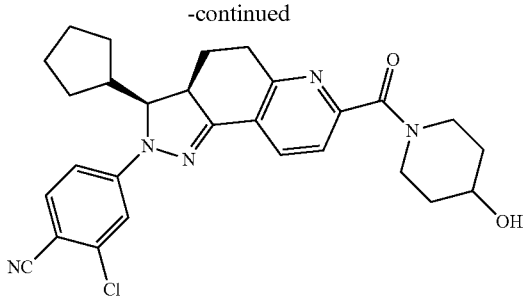

Compound of Formula (1)

To a 5 L reaction vessel were added (3S,3aR)-2-(3-chloro-4-cyanophenyl)-3-cyclopentyl-3,3a,4,5-tetrahydro-2H-pyrazolo[3,4-f]quinoline-7-carboxylic acid (380 g), dichloromethane (900 mL) and N,N-dimethylformamide (360 mL). Triethylamine (380 mL) was further added under stirring. The mixture was cooled to −10° C., and further stirred for 10 minutes. A solution (700 mL) of 4-hydroxypiperidine (137 g) in dichloromethane was added. The resulting mixture was stirred for 5 minutes. 2-(7-aza-1H-benzotriazole-1-yl)-1,1,3,3-tetramethyluronium hexafluorophosphate (HATU) (380 g) was added, and the reaction was conducted at room temperature for 3 hours. Then, 2-(7-aza-1H-benzotriazole-1-yl)-1,1,3,3-tetramethyluronium hexafluorophosphate (50 g) was additionally added, and the reaction was conducted for 1 hour. The solvent was removed under vacuum. The residue was dropwisely added to a 10-fold amount of water, and a solid was separated out. The solid was dissolved in dichloromethane (2 L), and washed with water (2 L) once. The aqueous phase was extracted with dichloromethane (500 mL) once. The organic phases were combined, dried and concentrated to dryness to produce a solid of Formula (1) (290 g), yield: 63.7%.

Molecular Formula: $C_{28}H_{30}ClN_5O_2$; MS (M+H): 504

$^1$H-NMR (CDCl$_3$, 400 MHz): δ 8.375-8.395 (1H, d), 7.423-7.474 (2H, m), 7.264-7.276 (1H, d), 6.968-6.995 (1H, dd), 4.641-4.678 (1H, dd), 4.17-4.21 (1H, m), 3.99 (1H, s), 3.76-3.79 (1H, m), 3.515 (1H, m), 3.41-3.44 (1H, m), 3.230-3.322 (2H, m), 2.995 (1H, m), 2.321-2.352 (1H, m), 2.10-2.15 (2H, m), 1.978-2.089 (2H, m), 1.863-1.895 (1H, m), 1.758-1.777 (1H, m), 1.433-1.663 (7H, m), 1.221-1.352 (2H, m).

Example 2: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo [3,4-f]quinolin-2-yl]benzonitrile (1)

The compound represented by formula (1) (1 g) as prepared in Example 1 was added in anhydrous ethanol (3 mL). The mixture was heated to 80° C. until the solution became clear. Then the mixture was slowly cooled to room temperature. The solid was filtered, and washed with anhydrous ethanol for three times. The resulting solid was dried at 60° C. under vacuum for 12 hours to produce Crystal Form I. The X-ray powder diffraction (XRD) spectrum of Crystal Form I was shown in FIG. 1, and its main parameters were as follows:

| 2θ angle Unit: degree (°) | d value Unit: angstrom | Strength Unit: % |
|---|---|---|
| 3.423 | 25.79197 | 2.2 |
| 4.571 | 19.31406 | 2.9 |
| 5.664 | 15.58973 | 3.1 |
| 8.343 | 10.58992 | 4.1 |
| 9.703 | 9.10809 | 47.6 |
| 10.764 | 8.21218 | 18.1 |
| 11.137 | 7.93840 | 16.5 |
| 12.122 | 7.29549 | 30.8 |
| 12.785 | 6.91833 | 48.9 |
| 14.690 | 6.02527 | 77.8 |
| 15.331 | 5.77476 | 39.2 |
| 16.834 | 5.26232 | 56.3 |
| 17.310 | 5.11893 | 100.0 |
| 17.987 | 4.92761 | 19.5 |
| 19.342 | 4.58548 | 71.7 |
| 19.639 | 4.51659 | 97.6 |
| 20.769 | 4.27346 | 11.5 |
| 21.191 | 4.18935 | 12.5 |
| 22.439 | 3.95900 | 40.0 |
| 23.159 | 3.83756 | 9.0 |
| 24.498 | 3.63081 | 21.9 |
| 26.103 | 3.41101 | 52.4 |
| 27.586 | 3.23093 | 20.4 |
| 29.564 | 3.01911 | 20.6 |
| 30.956 | 2.88642 | 12.0 |
| 31.954 | 2.79856 | 4.2 |
| 33.085 | 2.70537 | 4.9 |
| 33.516 | 2.67160 | 8.5 |
| 35.260 | 2.54333 | 4.0 |
| 35.946 | 2.49634 | 8.2 |
| 36.464 | 2.46209 | 9.4 |
| 37.729 | 2.38237 | 4.2 |
| 39.509 | 2.27904 | 6.2 |
| 40.615 | 2.21951 | 6.2 |
| 41.018 | 2.19865 | 6.8 |
| 42.503 | 2.12517 | 5.0 |
| 42.828 | 2.10982 | 6.0 |
| 44.139 | 2.05012 | 4.3 |

Example 3: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo [3,4-f]quinolin-2-yl]benzonitrile (2)

The compound represented by formula (1) (146 mg) as prepared in Example 1 was dissolved in acetonitrile (50 mL) at 80° C. The resulting mixture was then slowly cooled to room temperature, stirred overnight, and filtered to produce Crystal Form I.

Example 4: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo [3,4-f]quinolin-2-yl]benzonitrile (3)

The compound represented by formula (1) (200 mg) as prepared in Example 1 was added to a 100 mL round-bottom flask. Ethyl acetate (10 mL) was added. The mixture was heated to 78° C. under reflux. Then ethanol (0.5 mL) was added, and the mixture was stirred at 80° C. The resulting solution was slowly cooled to room temperature. After 2 days, the resulting mixture was filtered to produce Crystal Form I.

Example 5: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo [3,4-f]quinolin-2-yl]benzonitrile (4)

The compound represented by formula (1) (100 mg) as prepared in Example 1 was put in a 100 mL round-bottom flask. Acetone (3 mL) was added, and the compound was dissolved. To the resulting mixture was dropwisely added n-heptane (20 mL), and a solid separated out. The resulting mixture was filtered to produce Crystal Form I.

Example 6: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile (5)

The compound represented by formula (1) (100 mg) as prepared in Example 1 was added to a 100 mL round-bottom flask. A mixed solvent (0.5 mL, methanol:tetrahydrofuran=1:1) was added. The resulting mixture was heated to 60° C. Then the mixture was slowly cooled to room temperature, and a solid separated out. The resulting mixture was filtered to produce Crystal Form I.

Example 7: Preparation of Crystal Form I of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile (6)

The compound represented by formula (1) (100 mg) as prepared in Example 1 was added to a 100 mL round-bottom flask. A mixed solvent (3.5 mL, acetonitrile:acetone=1:1) was added to the round-bottom flask. The mixture was dissolved under heating at 60° C. and stirring, then slowly cooled to room temperature to separate out a solid. The resulting mixture was filtered to produce Crystal Form I

Example 8: Preparation of Crystal Form III of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile (1)

Figure 3:
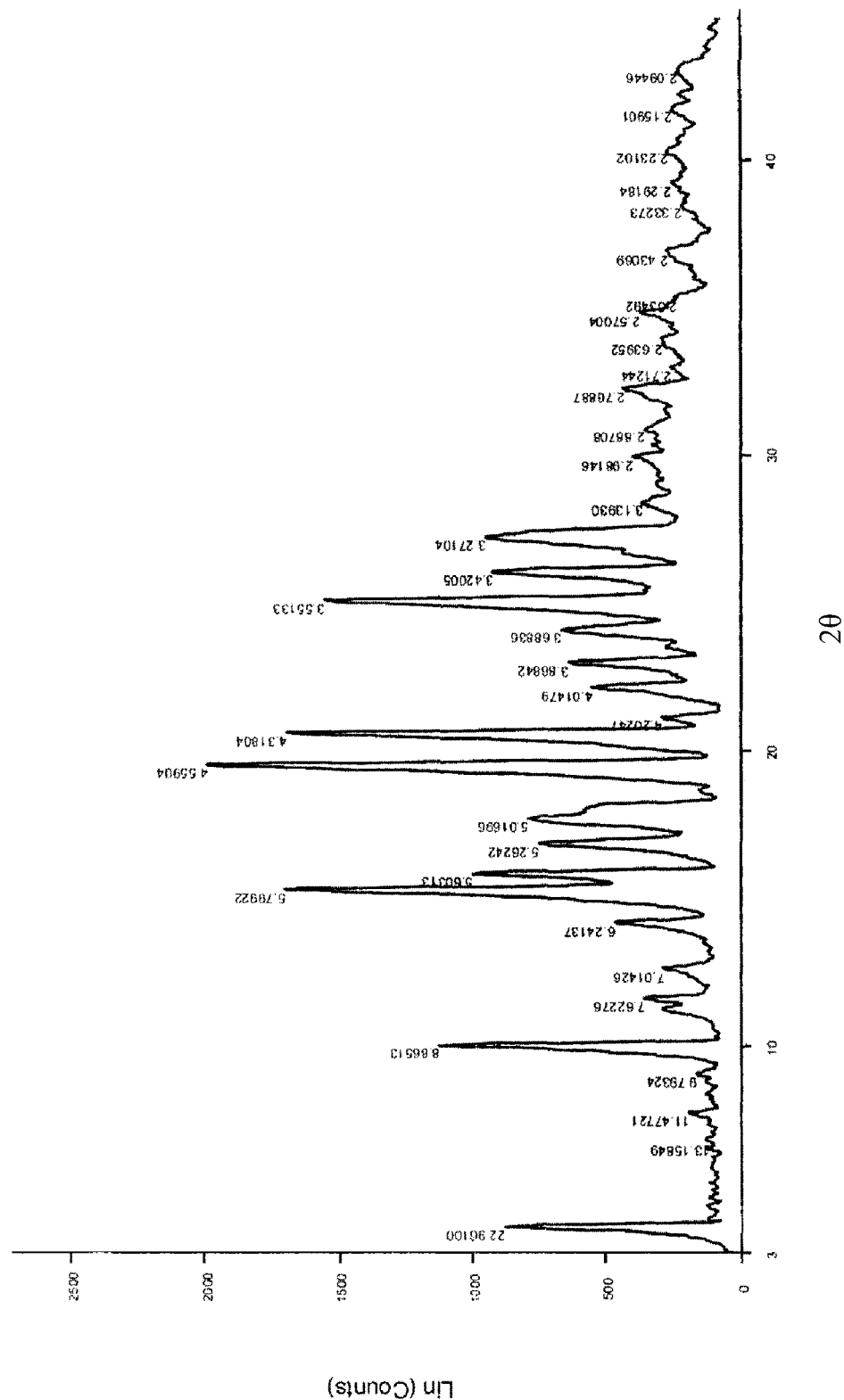
FIG. 3: the XRD spectrum for Crystal Form III of the compound of Formula (1)
Figure 4:
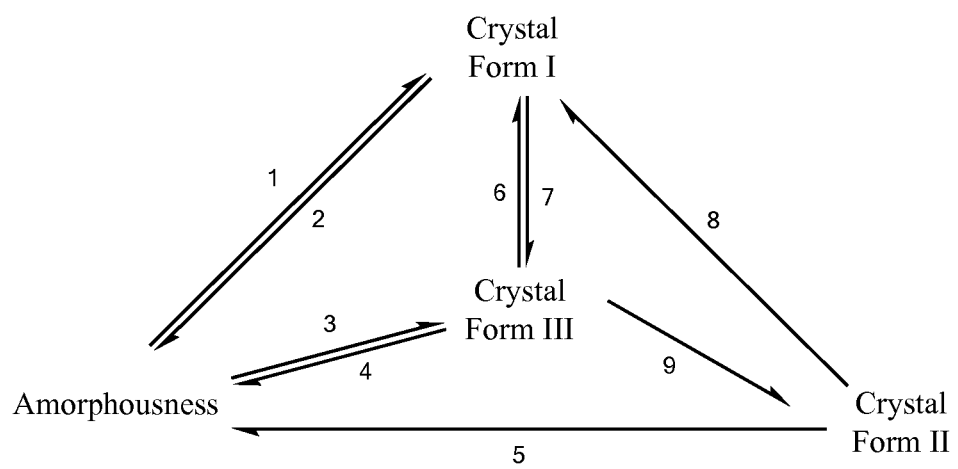

The compound represented by formula (1) (200 mg) as prepared in Example 1 was added to methanol (4 mL). The compound was dissolved at 80° C. The resulting solution was added dropwisely into water (40 mL). The resulting mixture was filtered to produce Crystal Form III. The X-ray powder diffraction (XRD) spectrum of Crystal Form III was shown in FIG. 3, and its main parameters were as follows:

| 2θ angle Unit: degree (°) | d value Unit: angstrom | Strength Unit: % |
|---|---|---|
| 3.845 | 22.96100 | 44.0 |
| 6.712 | 13.15849 | 5.8 |
| 7.697 | 11.47721 | 9.4 |
| 9.023 | 9.79324 | 8.1 |
| 9.970 | 8.86513 | 56.2 |
| 11.600 | 7.62276 | 17.7 |
| 12.610 | 7.01426 | 14.0 |
| 14.179 | 6.24137 | 23.1 |
| 15.266 | 5.79922 | 85.5 |
| 15.804 | 5.60313 | 49.9 |
| 16.834 | 5.26242 | 37.2 |
| 17.664 | 5.01696 | 39.5 |
| 19.455 | 4.55904 | 100.0 |
| 20.552 | 4.31804 | 85.1 |
| 21.124 | 4.20247 | 14.3 |
| 22.123 | 4.01479 | 27.4 |
| 22.972 | 3.86842 | 31.8 |
| 24.109 | 3.68836 | 33.2 |
| 25.055 | 3.55133 | 77.9 |
| 26.033 | 3.42005 | 46.2 |
| 27.241 | 3.27104 | 47.3 |
| 28.408 | 3.13930 | 17.9 |
| 29.946 | 2.98146 | 19.7 |
| 30.949 | 2.88708 | 17.5 |
| 32.306 | 2.76887 | 21.4 |
| 32.997 | 2.71244 | 12.5 |
| 33.935 | 2.63952 | 14.0 |
| 34.882 | 2.57004 | 18.4 |
| 35.381 | 2.53492 | 11.6 |
| 36.952 | 2.43069 | 13.1 |
| 38.563 | 2.33273 | 10.5 |
| 39.280 | 2.29184 | 12.5 |
| 40.396 | 2.23102 | 13.2 |
| 41.806 | 2.15901 | 12.4 |

Example 9: Preparation of Crystal Form III of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile (2)

The compound represented by formula (1) (100 mg) as prepared in Example 1 was added to a 10 mL centrifuge tube. A mixed solution (8 mL, water:acetonitrile=10:1) was added to the centrifuge tube, and stirred. The resulting mixture was filtered to produce Crystal Form III.

Example 10: Preparation of Crystal Form II of 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile Crystal Form III as prepared in Example 8 was dried for 12 hours under vacuum at room temperature to produce Crystal Form II. The X-ray powder diffraction (XRD) spectrum of Crystal Form II was shown in FIG. 2, and its main parameters were as follows:

| 2θ angle Unit: degree (°) | d value Unit: angstrom | Strength Unit: % |
|---|---|---|
| 3.574 | 24.70236 | 4.9 |
| 4.451 | 19.83656 | 56.2 |
| 7.515 | 11.75417 | 5.7 |
| 8.478 | 10.42104 | 28.0 |
| 9.002 | 9.81527 | 44.9 |
| 10.638 | 8.30970 | 23.2 |
| 12.216 | 7.23974 | 32.2 |
| 13.542 | 6.53344 | 20.0 |
| 14.049 | 6.29880 | 38.1 |
| 14.607 | 6.05934 | 90.9 |
| 16.422 | 5.39356 | 31.3 |
| 17.123 | 5.17422 | 26.2 |

-continued

| 2θ angle<br>Unit: degree (°) | d value<br>Unit: angstrom | Strength<br>Unit: % |
|---|---|---|
| 17.992 | 4.92615 | 56.8 |
| 18.695 | 4.74270 | 57.7 |
| 19.873 | 4.46396 | 100.0 |
| 21.230 | 4.18168 | 68.6 |
| 22.819 | 3.89399 | 28.9 |
| 24.589 | 3.61751 | 60.0 |
| 25.769 | 3.45445 | 26.8 |
| 26.520 | 3.35833 | 31.3 |
| 27.023 | 3.29690 | 28.0 |
| 28.447 | 3.13509 | 21.9 |
| 30.037 | 2.97262 | 10.2 |
| 30.853 | 2.89580 | 6.8 |
| 32.143 | 2.78249 | 7.7 |
| 34.206 | 2.61925 | 6.2 |
| 35.439 | 2.53088 | 5.7 |
| 36.144 | 2.48317 | 6.6 |
| 39.188 | 2.29700 | 6.6 |
| 40.726 | 2.21373 | 4.9 |
| 42.424 | 2.12895 | 6.5 |
| 43.393 | 2.08364 | 6.2 |

Assay 1: Stability for Crystal Form I of the Present Compound

Sample:

Crystal Form I of the compound represented by formula (1): Crystal Form I was prepared according to Example 2.

Test conditions for investigating the influencing factors:

High Temperature Tests:

(1) Crystal Form I of the compound represented by formula (1) was laid on a dry and clean watch glass, and kept at 60° C. for 10 days. Samples were taken respectively on Day 5 and Day 10. The contents of the relevant substance and the compound represented by formula (1) in the sample were measured, and compared with the contents of those in the sample taken on Day 0;

(2) Crystal Form I of the compound represented by formula (1) was packaged and sealed with a low-density polyethylene bag for pharmaceutical use in the inner layer and with a polyester/aluminum/polyethylene composite film for pharmaceutical package in the outer layer, and kept at 60° C. for 10 days. Samples were taken respectively on Day 5 and Day 10. The contents of the relevant substance and the compound represented by formula (1) in the sample were measured, and compared with the contents of those in the sample taken on Day 0.

High humidity test: Crystal Form I of the compound represented by formula (1) was laid on a dry and clean watch glass, and kept at 25° C. under a relative humidity of 90%±5% for 10 days. Samples were taken respectively on Day 5 and Day 10. The contents of the relevant substance and the compound represented by formula (1) in the sample were measured, and compared with the contents of those in the sample taken on Day 0.

Photostability test: Crystal Form I of the compound represented by formula (1) was laid on a dry and clean watch glass, and kept at an illuminance of 4500 Lx±500 Lx in an illumination box for 10 days. Samples were taken respectively on Day 5 and Day 10. The contents of the relevant substance and the compound represented by formula (1) in the sample were measured, and compared with the contents of those in the sample taken on Day 0.

Measurement of the Content of the Compound Represented by Formula (1)

The content of the compound represented by formula (1) was measured by using an external standard method in accordance with the High Performance Liquid Chromatography in Chinese Pharmacopoeia, Appendix V D, Edition 2010.

Measurement of the Content of the Relevant Substance

The content of the relevant substance was measured by using an area normalization method in accordance with the High Performance Liquid Chromatography in Chinese Pharmacopoeia, Appendix V D, Edition 2010.

Test results were shown in Table 1.

TABLE 1

The investigation results of the influencing factor tests for Crystal Form I of the compound represented by formula (1)

| Conditions | Day | Content of the compound represented by formula (1) (%) | Content of the relevant substance (%) |
|---|---|---|---|
|  | 0 | 99.5 | 0.54 |
| 60° C.-(1) | 5 | 98.9 | 0.82 |
|  | 10 | 98.1 | 0.97 |
| 60° C.-(2) | 5 | 99.7 | 0.58 |
|  | 10 | 99.0 | 0.60 |
| RH90% ± 5% | 5 | 99.1 | 0.56 |
|  | 10 | 99.0 | 0.56 |
| 4500 Lx ± 500 Lx | 5 | 98.1 | 1.2 |
|  | 10 | 97.0 | 2.0 |

The present inventors investigated the stability of Crystal Form I of the compound represented by formula (1). It could be clear from the investigation results that the contents of the relevant substance and the compound represented by formula (1) in Crystal Form I of the compound represented by formula (1) substantially did not change at a high temperature, at a high humidity and under an illumination condition. Crystal form I was superior to the amorphous form in the stability, which showed that Crystal Form I of the compound represented by formula (1) had a relatively high stability that was suitable for drug manufacture, storage and transport and was favorable for ensuring the validity and the safety in the drug use.

Assay 2

Stability for Crystal Form II of the present compound

Sample:

Crystal Form II of the compound represented by formula (1): Crystal Form II was prepared according to Example 4.

Test Conditions for Investigating the Influencing Factors:

High Temperature Tests:

(1) Crystal Form II of the compound represented by formula (1) was laid on a dry and clean watch glass, and kept at 60° C. for 10 days. Sample was taken on Day 10. The contents of the relevant substance and the compound represented by formula (1) in the sample were measured, and compared with the contents of those in the sample taken on Day 0;

(2) Crystal Form II of the compound represented by formula (1) was packaged and sealed with a low-density polyethylene bag for pharmaceutical use in the inner layer and with a polyester/aluminum/polyethylene composite film for pharmaceutical package in the outer layer, and kept at 60° C. for 10 days. Sample was taken on Day 10. The contents of the relevant substance and the compound represented by formula (1) in the sample were measured, and compared with the contents of those in the sample taken on Day 0.

High humidity test: Crystal Form II of the compound represented by formula (1) was laid on a dry and clean watch glass, and kept at 25° C. under a relative humidity of 90%±5% for 10 days. Sample was taken respectively on Day 10. The contents of the relevant substance and the compound represented by formula (1) in the sample were measured, and compared with the contents of those in the sample taken on Day 0.

Photostability test: Crystal Form II of the compound represented by formula (1) was laid on a dry and clean watch glass, and kept at an illuminance of 5000 Lx±500 Lx in an illumination box for 10 days. Sample was taken on Day 10. The contents of the relevant substance and the compound represented by formula (1) in the sample were measured, and compared with the contents of those in the sample taken on Day 0.

Measurement of the Content of the Compound Represented by Formula (1)

The content of the compound represented by formula (1) was measured by using an external standard method in accordance with the High Performance Liquid Chromatography in Chinese Pharmacopoeia, Appendix V D, Edition 2010.

Measurement of the Content of the Relevant Substance

The content of the relevant substance was measured by using an area normalization method in accordance with the High Performance Liquid Chromatography in Chinese Pharmacopoeia, Appendix V D, Edition 2010.

Test results were shown in Table 2.

TABLE 2

The investigation results of the influencing factor tests for Crystal Form II of the compound represented by formula (1)

| Condition | Day | Content of the compound represented by formula (1) (%) | Content of the relevant substance (%) |
|---|---|---|---|
|  | 0 | 96.2 | 2.6 |
| 60° C.-(1) | 10 | 96.2 | 2.8 |
| 60° C.-(2) | 10 | 97.1 | 2.7 |
| RH90% ± 5% | 10 | 96.9 | 2.6 |
| 5000 Lx ± 500 Lx | 10 | 95.5 | 2.8 |

The present inventors investigated the stability of Crystal Form II of the compound represented by formula (1). It could be clear from the investigation results that the contents of the relevant substance and the compound represented by formula (1) in Crystal Form II of the compound represented by formula (1) substantially did not change at a high temperature, at a high humidity and under an illumination condition. Crystal form II was superior to the amorphous form in the stability, which showed that Crystal Form II of the compound represented by formula (1) had a relatively high stability that was suitable for drug manufacture, storage and transport and was favorable for ensuring the validity and the safety in the drug use.

Assay 3

Organ protection and depressurization effect of Crystal Form I of the present invention on the high salt induced Dahl salt sensitive (Dahl/SS) rats Sample and Sample Preparation:

The solid dispersion of Crystal Form I of the present invention (Crystal Form I of the present invention: PVPK30=1:8 (w/w)): the solid dispersion of Crystal Form I of the present invention was formulated with a suitable amount of sterile water for injection into suspensions having concentrations of 0.03, 0.10, 0.30, and 1.00 mg/mL. The suspension was prepared before use every day.

Animal Group and Model:

Experiment animals: male Dahl/ss rats of SPF (specific pathogen free)-grade, 8-9 weeks, purchased via Vital River Laboratories from HARLAN LABORATORIES, INC. After one week normal quarantine, rats in good sign and condition were used in the experiment.

Dahl/ss rats were randomly divided into six groups according to the blood pressure measurement before administration:

Normal control (n=10),

Model group (4% NaCl, n=12),

Treatment groups with Crystal Form I of the present invention, four groups:

The treatment group with 0.3 mg/kg/day (n=11),

The treatment group with 1 mg/kg/day (n=11),

The treatment group with 3 mg/kg/day (n=11),

The treatment group with 10 mg/kg/day (n=11), n is the rat number.

Experiment Method:

The in vivo pharmacodynamic activity of Crystal Form I of the present invention was evaluated by the hypertension and kidney injury Dahl/ss rat's model.

One week before the experiment, the blood pressures of rats were monitored twice by the tail-cuff blood pressure measurement so that the rats could accommodate the blood pressure monitoring operation. The blood pressures of rats were monitored once before starting the experiment and used as the basic blood pressures before administration. The rats were randomly divided into groups according to the measured blood pressures before administration. The model was established by feeding the rats with a high salt chow (AIN-93G experiment animal feed containing 4% NaCl) for 42 days, in which the rats were freely accessible to food and water. And rats in control group were fed with a low-sodium chow.

The rats in the treatment groups with Crystal Form I of the present invention were respectively administrated with Crystal Form I of the present invention in a dosage of 0.3, 1, 3, and 10 mg/kg/day. Rats in treatment groups were dosed orally via gavage twice a day by 5 mL/kg. The rats in the model group and in the normal control were administrated with the same volume of sterile water for injection.

Blood pressure (systolic blood pressure, abbreviated as SBP) measurement: The blood pressure was measured once each week for six weeks. The blood pressure changes were analyzed for each group.

The pathological examinations for kidney and heart: After the experiment, the rats were killed in a painless manner. The heart and the bilateral kidneys were collected for histopathology analysis. Kidney injury was scored and semi-quantitatively analyzed based on hematoxylin-eosin (HE) stain. The heart injury was analyzed by the measurement of left ventricular wall thickness.

Experiment Result:

Depressurization effect: it could be seen that Crystal Form I of the present invention showed a significant depressurization effect in the model and presented a certain dose-dependent relationship (Table 3).

TABLE 3

| | | SBP (mmHg, mean ± SD) | |
|---|---|---|---|
| Group | | Before Administration | After Administration (on 41$^{th}$ day) |
| Normal control | | 139.3 ± 13.4 | 149.4 ± 9.6 |
| Model group | | 139.9 ± 10.7 | 183.0 ± 12.8* |
| Crystal Form I of the present compound | 0.3 mg/kg/day | 140.8 ± 9.6 | 166.5 ± 10.2*# |
| Crystal Form I of the present compound | 1 mg/kg/day | 140.9 ± 9.5 | 148.7 ± 9.6# |
| Crystal Form I of the present compound | 3 mg/kg/day | 141.0 ± 9.4 | 141.6 ± 8.0# |
| Crystal Form I of the present compound | 10 mg/kg/day | 141.2 ± 9.2 | 141.2 ± 9.6# |

*p < 0.05, compared with normal control;
p < 0.05, compared with model group.

Kidney and heart protections: According to the kidney injury scores, the treatment groups with Crystal Form I of the present invention showed a remarkable prevention from the increase in the kidney injury score (Table 4). Compared with the model group, Crystal Form I of the present invention significantly decreased the left ventricular wall thickness (Table 4).

TABLE 4

| | Protection for kidney injury and heart injury | | |
|---|---|---|---|
| Group | | Kidney injury scores (Mean ± SD) | left ventricular wall thickness (cm, mean ± SD) |
| Normal control | | 0.93 ± 0.079 | 0.401 ± 0.014 |
| Model group | | 2.05 ± 0.091* | 0.410 ± 0.026 |
| Crystal Form I of the present invention | 0.3 mg/kg/day | 2.02 ± 0.268* | 0.392 ± 0.024 |
| Crystal Form I of the present invention | 1 mg/kg/day | 1.25 ± 0.428# | 0.383 ± 0.017# |
| Crystal Form I of the present invention | 3 mg/kg/day | 1.84 ± 0.596* | 0.381 ± 0.026# |
| Crystal Form I of the present invention | 10 mg/kg/day | 1.71 ± 0.719* | 0.383 ± 0.019# |

*p < 0.05, compared with normal control;
p < 0.05, compared with model group.

In the hypertension and nephrosis models of the high salt induced Dhal/ss rats, Crystal Form I of the present invention showed remarkable depressurization effect and kidney injury protection.

We claim:

1. A crystal form of a compound represented by formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile, which is obtainable from subjecting (3S,3aR)-2-(3-chloro-4-cyanophenyl)-3-cyclopentyl-3,3a,4,5-tetrahydro-2H-pyrazolo[3,4-f]quinoline-7-carboxylic acid and 4-hydroxypiperidine to a condensation reaction,

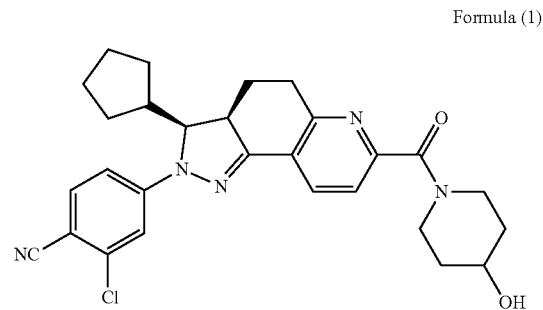 [SMILES: N#Cc1ccc(N2N=C3c4ccc(C(=O)N5CCC(O)CC5)nc4CC[C@@H]3[C@@H]2C2CCCC2)cc1Cl]

Formula (1)

which is characterized by having an X-ray powder diffraction pattern comprising the following characteristic peaks expressed by 2θ degree, when measured using CuKa radiation:

Crystal Form I: 9.8°±0.2°, 12.9°±0.2°, 14.8°±0.2°, 15.4°±0.2°, 16.9°±0.2°, 17.4°±0.2°, 19.4°±0.2°, 19.8°±0.2°, 22.6°±0.2°, 26.2°±0.2°;

Crystal Form II: 4.5°±0.2°, 9.0°±0.2°, 12.2°±0.2°, 14.0°±0.2°, 14.6°±0.2°, 18.0°±0.2°, 18.7°±0.2°, 19.9°±0.2°, 21.2°±0.2°, 24.6°±0.2°.

Figure 2:
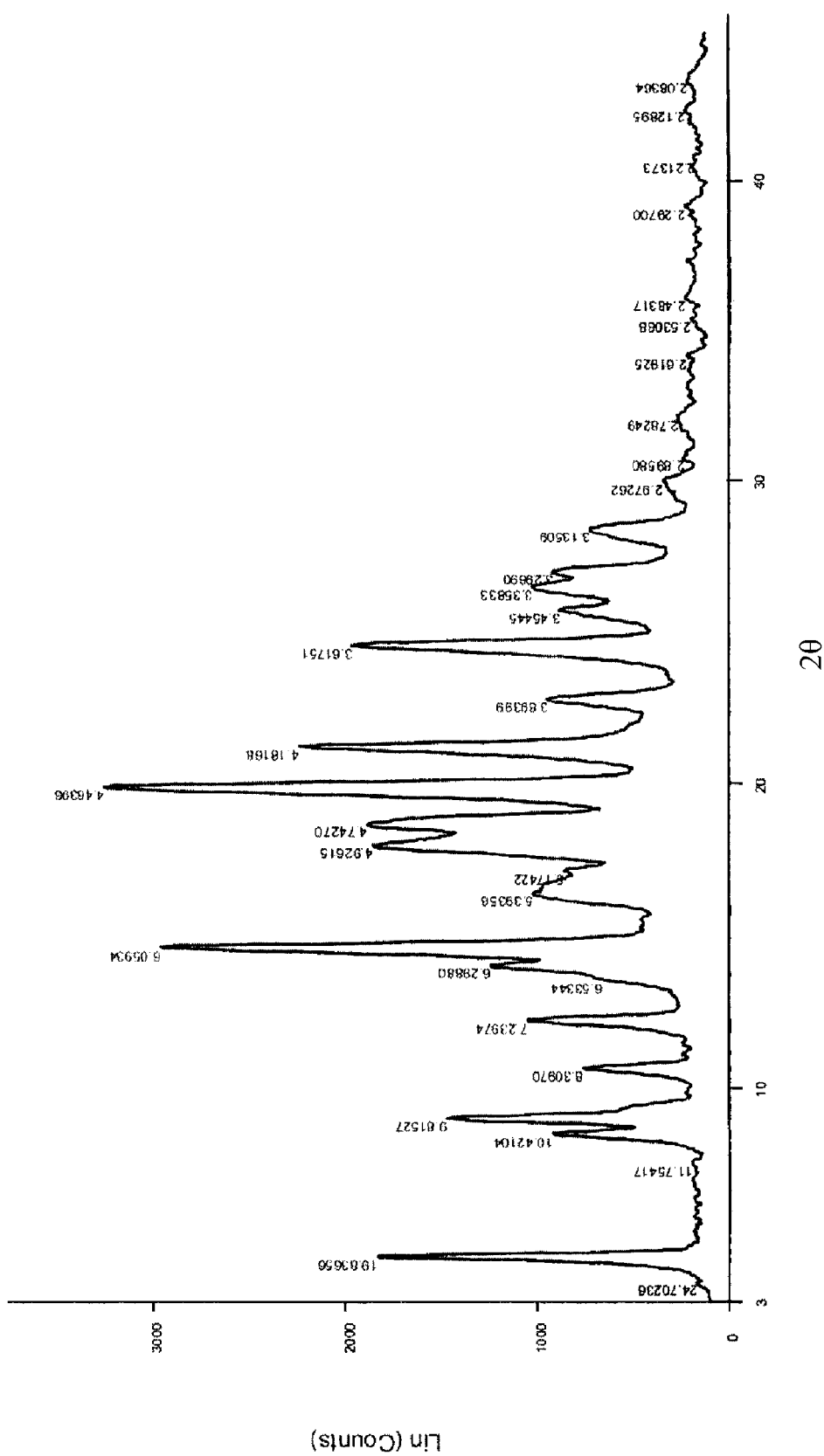
FIG. 2: the XRD spectrum for Crystal Form II of the compound of Formula (1)

2. The crystal form of the compound of claim 1, wherein the crystal form is Crystal Form I or Crystal Form II; Crystal Form I having an XRD spectrum when measured using CuKa radiation as shown in FIG. 1; and Crystal Form II having an XRD spectrum when measured using CuKa radiation as shown in FIG. 2.

3. A process for preparing a crystal form of a compound represented by formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile,

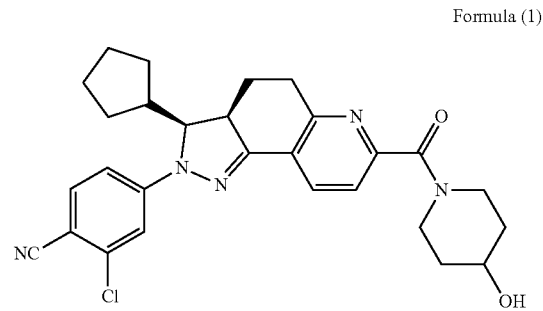 [SMILES: N#Cc1ccc(N2N=C3c4ccc(C(=O)N5CCC(O)CC5)nc4CC[C@@H]3[C@@H]2C2CCCC2)cc1Cl]

Formula (1)

wherein the crystal form is the Crystal Form I or the Crystal Form II of the compound represented by formula (1) of claim 1;
comprising the steps of:
(9) Chirally resolving ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-ethyl 2-(3-chloro-4-cyanophenyl)-3-cyclopentyl-3,3a,4,5-tetrahydro-2H-pyrazolo[3,4-f]quinoline-7-carboxylate;
(10) Hydrolyzing (3S,3aR)-ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-2-(3-chloro-4-cyanophenyl)-3-cyclopentyl-3,3a,4,5-tetrahydro-2H-pyrazolo[3,4-f]quinoline-7-carboxylic acid;
(11) Subjecting (3S,3aR)-2-(3-chloro-4-cyanophenyl)-3-cyclopentyl-3,3a,4,5-tetrahydro-2H-pyrazolo[3,4-f]

quinoline-7-carboxylic acid and 4-hydroxypiperidine to a condensation reaction to produce the compound represented by formula (1);

said process further comprises one of the following steps:

placing the compound represented by formula (1) obtained in the step (11) in anhydrous methanol, anhydrous ethanol, anhydrous n-propanol, acetonitrile, a mixed solvent of ethyl acetate and ethanol, a mixed solvent of methanol and tetrahydrofuran, or a mixed solvent of acetonitrile and acetone, heating the resulting solution until it becomes clear, then cooling the resulting solution to separate out a solid, and filtering and drying the separated solid;

dissolving the compound represented by formula (1) obtained in the step (11) in acetone, adding the resulting solution dropwisely to n-heptane, and filtering the resulting mixture;

placing the compound represented by formula (1) obtained in the step (11) in methanol, ethanol, or n-propanol to dissolve it, then adding the resulting solution dropwisely to water, filtering the resulting mixture, and drying the filtered substance under vacuum; or washing the compound represented by formula (1) obtained in the step (11) with a mixed solution of water and acetonitrile, filtering the resulting mixture, and drying the filtered substance under vacuum.

4. A process for preparing a crystal form of a compound represented by formula (1), 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile,

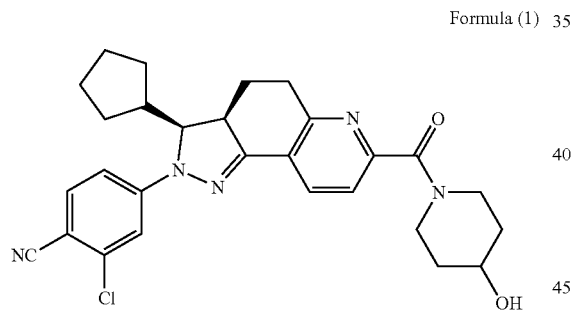

Formula (1)

wherein the crystal form is the Crystal Form I or the Crystal Form II of the compound represented by formula (1) of claim 2;

comprising the steps of:

(9) Chirally resolving ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-ethyl 2-(3-chloro-4-cyanophenyl)-3-cyclopentyl-3,3a,4,5-tetrahydro-2H-pyrazolo[3,4-f]quinoline-7-carboxylate;

(10) Hydrolyzing (3S,3aR)-ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-2-(3-chloro-4-cyanophenyl)-3-cyclopentyl-3,3a,4,5-tetrahydro-2H-pyrazolo[3,4-f]quinoline-7-carboxylic acid;

(11) Subjecting (3S,3aR)-2-(3-chloro-4-cyanophenyl)-3-cyclopentyl-3,3a,4,5-tetrahydro-2H-pyrazolo[3,4-f]quinoline-7-carboxylic acid and 4-hydroxypiperidine to a condensation reaction to produce the compound represented by formula (1);

the process further comprises one of the following steps:

placing the compound represented by formula (1) obtained in the step (11) in anhydrous methanol, anhydrous ethanol, anhydrous n-propanol, acetonitrile, a mixed solvent of ethyl acetate and ethanol, a mixed solvent of methanol and tetrahydrofuran, or a mixed solvent of acetonitrile and acetone, heating the resulting solution until it becomes clear, then cooling the resulting solution to separate out a solid, and filtering and drying the separated solid;

dissolving the compound represented by formula (1) obtained in the step (11) in acetone, adding the resulting solution dropwisely to n-heptane, and filtering the resulting mixture;

placing the compound represented by formula (1) obtained in the step (11) in methanol, ethanol, or n-propanol to dissolve it, then adding the resulting solution dropwisely to water, filtering the resulting mixture, and drying the filtered substance under vacuum; or washing the compound represented by formula (1) obtained in the step (11) with a mixed solution of water and acetonitrile, filtering the resulting mixture, and drying the filtered substance under vacuum.

5. The process of claim 3, further comprising the steps of:

(1) Subjecting 1,3-cyclohexanedione, ammonium acetate and acrolein to condensation and addition reactions to produce 5-oxo-5,6,7,8-tetrahydroquinoline;

(2) Subjecting 5-oxo-5,6,7,8-tetrahydroquinoline to an oxidation reaction to produce 5-oxo-5,6,7,8-tetrahydroquinoline-N-oxide;

(3) Subjecting 5-oxo-5,6,7,8-tetrahydroquinoline-N-oxide, N,N-dimethylcarbamic chloride, and trimethylsilylcyanide to a substitution reaction to produce 5-oxo-5,6,7,8-tetrahydroquinoline-2-carbonitrile;

(4) Subjecting 5-oxo-5,6,7,8-tetrahydroquinoline-2-carbonitrile to hydrolysis and esterification reactions to produce ethyl 5-oxo-5,6,7,8-tetrahydroquinoline-2-carboxylate;

(5) Subjecting ethyl 5-oxo-5,6,7,8-tetrahydroquinoline-2-carboxylate and cyclopentanecarbaldehyde to a condensation reaction to produce (E)-ethyl 6-cyclopentylmethylene-5-oxo-5,6,7,8-tetrahydroquinoline-2-carboxylate;

(6) Subjecting 2-chloro-4-fluorobenzonitrile and hydrazine hydrate to a substitution reaction to produce 2-chloro-4-hydrazinobenzonitrile;

(7) Subjecting 2-chloro-4-hydrazinobenzonitrile and hydrochloric acid to a salt forming reaction to produce 2-chloro-4-hydrazinobenzonitrile hydrochloride;

(8) Subjecting (E)-ethyl 6-cyclopentylmethylene-5-oxo-5,6,7,8-tetrahydroquinoline-2-carboxylate and 2-chloro-4-hydrazinobenzonitrile hydrochloride to a condensation reaction to produce ethyl 2-(3-chloro-4-cyanophenyl)-3-cyclopentyl-3,3a,4,5-tetrahydro-2H-pyrazolo[3,4-f]quinoline-7-carboxylate;

(9) Chirally resolving ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-ethyl 2-(3-chloro-4-cyanophenyl)-3-cyclopentyl-3,3a,4,5-tetrahydro-2H-pyrazolo[3,4-f]quinoline-7-carboxylate;

(10) Hydrolyzing (3S,3aR)-ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-2-(3-chloro-4-cyanophenyl)-3-cyclopentyl-3,3a,4,5-tetrahydro-2H-pyrazolo[3,4-f]quinoline-7-carboxylic acid;

(11) Subjecting (3S,3aR)-2-(3-chloro-4-cyanophenyl)-3-cyclopentyl-3,3a,4,5-tetrahydro-2H-pyrazolo[3,4-f]quinoline-7-carboxylic acid and 4-hydroxypiperidine to a condensation reaction to produce the compound represented by formula (1);

the process further comprises one of the following steps:
placing the compound represented by formula (1) obtained in the step (11) in anhydrous methanol, anhydrous ethanol, anhydrous n-propanol, acetonitrile, a mixed solvent of ethyl acetate and ethanol, a mixed solvent of methanol and tetrahydrofuran, or a mixed solvent of acetonitrile and acetone, heating the resulting solution until it becomes clear, then cooling the resulting solution to separate out a solid, and filtering and drying the separated solid;

dissolving the compound represented by formula (1) obtained in the step (11) in acetone, adding the resulting solution dropwisely to n-heptane, and filtering the resulting mixture;

placing the compound represented by formula (1) obtained in the step (11) in methanol, ethanol, or n-propanol to dissolve it, then adding the resulting solution dropwisely to water, filtering the resulting mixture, and drying the filtered substance under vacuum; or washing the compound represented by formula (1) obtained in the step (11) with a mixed solution of water and acetonitrile, filtering the resulting mixture, and drying the filtered substance under vacuum.

6. The process of claim 4, further comprising the steps of:
(1) Subjecting 1,3-cyclohexanedione, ammonium acetate and acrolein to condensation and addition reactions to produce 5-oxo-5,6,7,8-tetrahydroquinoline;
(2) Subjecting 5-oxo-5,6,7,8-tetrahydroquinoline to an oxidation reaction to produce 5-oxo-5,6,7,8-tetrahydroquinoline-N-oxide;
(3) Subjecting 5-oxo-5,6,7,8-tetrahydroquinoline-N-oxide, N,N-dimethylcarbamic chloride, and trimethylsilylcyanide to a substitution reaction to produce 5-oxo-5,6,7,8-tetrahydroquinoline-2-carbonitrile;
(4) Subjecting 5-oxo-5,6,7,8-tetrahydroquinoline-2-carbonitrile to hydrolysis and esterification reactions to produce ethyl 5-oxo-5,6,7,8-tetrahydroquinoline-2-carboxylate;
(5) Subjecting ethyl 5-oxo-5,6,7,8-tetrahydroquinoline-2-carboxylate and cyclopentanecarbaldehyde to a condensation reaction to produce (E)-ethyl 6-cyclopentylmethylene-5-oxo-5,6,7,8-tetrahydroquinoline-2-carboxylate;
(6) Subjecting 2-chloro-4-fluorobenzonitrile and hydrazine hydrate to a substitution reaction to produce 2-chloro-4-hydrazinobenzonitrile;
(7) Subjecting 2-chloro-4-hydrazinobenzonitrile and hydrochloric acid to a salt forming reaction to produce 2-chloro-4-hydrazinobenzonitrile hydrochloride;
(8) Subjecting (E)-ethyl 6-cyclopentylmethylene-5-oxo-5,6, 7, 8-tetrahydroquinoline-2-carboxylate and 2-chloro-4-hydrazinobenzonitrile hydrochloride to a condensation reaction to produce ethyl 2-(3-chloro-4-cyanophenyl)-3-cyclopentyl-3,3a,4,5-tetrahydro-2H-pyrazolo[3,4-f]quinoline-7-carboxylate;
(9) Chirally resolving ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-ethyl 2-(3-chloro-4-cyanophenyl)-3-cyclopentyl-3,3a,4,5-tetrahydro-2H-pyrazolo[3,4-f]quinoline-7-carboxylate;
(10) Hydrolyzing (3S,3aR)-ethyl 2-(3-chloro-4-cyanophenyl)-3-cyclopentyl-3,3a,4,5-tetrahydro-2H-pyrazolo[3,4-f]quinoline-7-carboxylate to produce (3S,3aR)-2-(3-chloro-4-cyanophenyl)-3-cyclopentyl-3,3a,4,5-tetrahydro-2H-pyrazolo[3,4-f]quinoline-7-carboxylic acid;
(11) Subjecting (3S,3aR)-2-(3-chloro-4-cyanophenyl)-3-cyclopentyl-3,3a,4,5-tetrahydro-2H-pyrazolo[3,4-f]quinoline-7-carboxylic acid and 4-hydroxypiperidine to a condensation reaction to produce the compound represented by formula (1);

the process further comprises one of the following steps:
placing the compound represented by formula (1) obtained in the step (11) in anhydrous methanol, anhydrous ethanol, anhydrous n-propanol, acetonitrile, a mixed solvent of ethyl acetate and ethanol, a mixed solvent of methanol and tetrahydrofuran, or a mixed solvent of acetonitrile and acetone, heating the resulting solution until it becomes clear, then cooling the resulting solution to separate out a solid, and filtering and drying the separated solid;

dissolving the compound represented by formula (1) obtained in the step (11) in acetone, adding the resulting solution dropwisely to n-heptane, and filtering the resulting mixture;

placing the compound represented by formula (1) obtained in the step (11) in methanol, ethanol, or n-propanol to dissolve it, then adding the resulting solution dropwisely to water, filtering the resulting mixture, and drying the filtered substance under vacuum; or washing the compound represented by formula (1) obtained in the step (11) with a mixed solution of water and acetonitrile, filtering the resulting mixture, and drying the filtered substance under vacuum.

7. A process for preparing Crystal Form I of the compound represented by formula (1) of claim 1, comprising placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in anhydrous methanol, anhydrous ethanol, anhydrous n-propanol, acetonitrile, a mixture of ethyl acetate and ethanol, a mixture of methanol and tetrahydrofuran, or a mixture of acetonitrile and acetone, heating the resulting solution until it becomes clear, then cooling the resulting solution to separate out a solid, and filtering and drying the separated solid to produce Crystal Form I; or dissolving the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in acetone, adding the resulting solution dropwisely to n-heptane, and filtering the resulting mixture to produce Crystal Form I.

8. A process for preparing Crystal Form I of the compound represented by formula (1) of claim 2, comprising placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in anhydrous methanol, anhydrous ethanol, anhydrous n-propanol, acetonitrile, a mixture of ethyl acetate and ethanol, a mixture of methanol and tetrahydrofuran, or a mixture of acetonitrile and acetone, heating the resulting solution until it becomes clear, then cooling the resulting solution to separate out a solid, and filtering and drying the separated solid to produce Crystal Form I; or dissolving the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in acetone, adding the resulting solution dropwisely to n-heptane, and filtering the resulting mixture to produce Crystal Form I.

9. A process for preparing Crystal Form II of the compound represented by formula (1) of claim 1, comprising placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in methanol, ethanol, or n-propanol to dissolve it, then adding the resulting solution dropwisely to water, and filtering the resulting mixture to produce the resulting Crystal Form III; or washing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile with a mixture of water and acetonitrile, and filtering the resulting mixture to produce the resulting Crystal Form III; then drying the resulting Crystal Form III under vacuum to produce Crystal Form II.

10. A process for preparing Crystal Form II of the compound represented by formula (1) of claim 2, comprising placing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile in methanol, ethanol, or n-propanol to dissolve it, then adding the resulting solution dropwisely to water, and filtering the resulting mixture to produce the resulting Crystal Form III; or washing the compound 2-chloro-4-[(3S,3aR)-3-cyclopentyl-7-(4-hydroxypiperidin-1-carbonyl)-3,3a,4,5-tetrahydro-2H-pyrazolo[3,4-f]quinolin-2-yl]benzonitrile with a mixture of water and acetonitrile, and filtering the resulting mixture to produce the resulting Crystal Form III; then drying the resulting Crystal Form III under vacuum to produce Crystal Form II.

11. A pharmaceutical composition comprising the crystal form of the compound represented by formula (1) of claim 1, and a pharmaceutically acceptable carrier, wherein the crystal form is Crystal Form I, Crystal Form II or a combination thereof.

12. A pharmaceutical composition comprising the crystal form of the compound represented by formula (1) of claim 2, and a pharmaceutically acceptable carrier, wherein the crystal form is Crystal Form I, Crystal Form II or a combination thereof.

13. The pharmaceutical composition of claim 11 for treating and/or preventing kidney injury or cardiovascular disease, wherein the crystal form is Crystal Form I, Crystal Form II or a combination thereof.

14. The pharmaceutical composition of claim 12 for treating and/or preventing kidney injury or cardiovascular disease, wherein the crystal form is Crystal Form I, Crystal Form II or a combination thereof.

15. The pharmaceutical composition of claim 13, wherein the cardiovascular disease comprises heart injury, hypertension, heart failure, myocardial infarction, angina pectoris, cardiac hypertrophy, myocarditis, fibrosis of heart and blood vessel, baroceptor dysfunction or arrhythmia.

16. The pharmaceutical composition of claim 14, wherein the cardiovascular disease comprises heart injury, hypertension, heart failure, myocardial infarction, angina pectoris, cardiac hypertrophy, myocarditis, fibrosis of heart and blood vessel, baroceptor dysfunction or arrhythmia.

* * * * *

UNITED STATES PATENT AND TRADEMARK OFFICE
CERTIFICATE OF CORRECTION

PATENT NO. : 9,809,589 B2
APPLICATION NO. : 14/653933
DATED : November 7, 2017
INVENTOR(S) : Chen Jiang et al.

It is certified that error appears in the above-identified patent and that said Letters Patent is hereby corrected as shown below:

On the Title Page

Item (56) At Column 2, Line number 19-20, please amend as follows, "CN201380066871.7, "Notice to Grant Patent Right for Invention with English Translation", dated Sep. 5, 2016, 5 pages."

Signed and Sealed this
Second Day of April, 2024

Katherine Kelly Vidal
*Director of the United States Patent and Trademark Office*